(12) United States Patent
Haaring

(10) Patent No.: US 9,650,645 B2
(45) Date of Patent: May 16, 2017

(54) CUCUMBER WITH INCREASED NUMBER OF FRUITS

(71) Applicant: RIJK ZWAAN ZAADTEELT EN ZAADHANDEL B.V., De Lier (NL)

(72) Inventor: Cornelis Haaring, Maasland (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 13/793,050

(22) Filed: Mar. 11, 2013

(65) Prior Publication Data

US 2013/0269048 A1    Oct. 10, 2013

(30) Foreign Application Priority Data

Mar. 9, 2012   (EP) .................... 12158714

(51) Int. Cl.
  *A01H 5/08*   (2006.01)
  *A01H 5/00*   (2006.01)
  *C12N 15/82*  (2006.01)
  *A01H 1/00*   (2006.01)

(52) U.S. Cl.
  CPC .......... *C12N 15/8261* (2013.01); *A01H 1/00* (2013.01); *A01H 5/00* (2013.01); *A01H 5/08* (2013.01)

(58) Field of Classification Search
  None
  See application file for complete search history.

(56) References Cited

U.S. PATENT DOCUMENTS

| 8,710,303 B2 | 4/2014 | Crienen et al. |
| 2011/0047642 A1 | 2/2011 | Crienen et al. |

FOREIGN PATENT DOCUMENTS

WO   2009/059777   5/2009

OTHER PUBLICATIONS

Shetty and Wehner 2002 Crop Science 42, 6:2174-2183.*
Fazio et al 2003 Theor. App. Genet 107:864-874.*
European Search Report dated Jul. 31, 2012, which issued during prosecution of European Application No. EP 12 15 8714.
Christopher S. Cramer, et al. "Fruit Yield and Yield Component Means and Correlations of Four Slicing Cucumber Populations Improved through Six to Ten Cycles of Recurrent Selection" Journal of the American Society for Horticultural Science 123(3):388-395, May 1998.
Christopher S. Cramer, et al. "Path Analysis of the Correlation between Fruit Number and Plant Traits of Cucumber Populations" HortScience 35(4):708-711, Jul. 2000.
Jack E. Staub, et al. "Cucumber" Handbook of Plant Breeding: Vegetables, Springer Science+Business Media, LLC, pp. 241-282, Jan. 2008.
Todd C. Wehner. "Breeding for Improved Yield in Cucumber" Plant Breeding Reviews 6:323-359, Jan. 1989.

* cited by examiner

*Primary Examiner* — Brent Page
(74) *Attorney, Agent, or Firm* — Vedder Price P.C.; Thomas J. Kowalski; Deborah L. Lu

(57) ABSTRACT

The present invention relates to a cucumber plant (*Cucumis sativus*) which may comprise genetic information that results in an increase in the number of fruits. The invention also relates to the seeds and progeny of such plants and to propagation material for obtaining such plants. Furthermore the invention relates to the use of the plants, seeds and propagation material that may comprise the genetic information as germplasm in a breeding program.

6 Claims, 1 Drawing Sheet

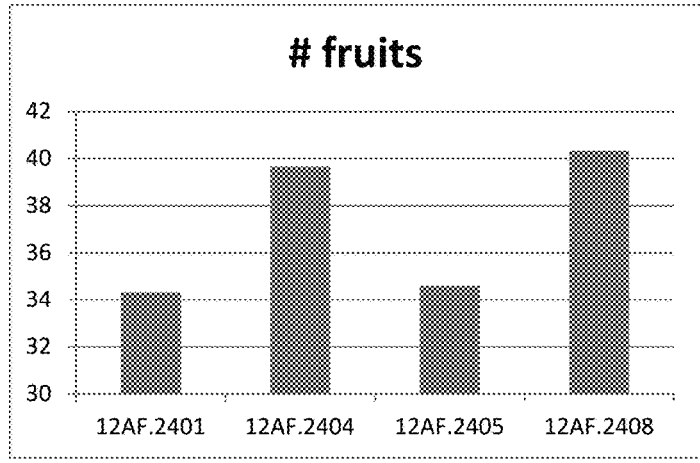

| 12AF.2401 | F1 | no little leaf genes |
| 12AF.2404 | F1 | isogenic to 2401, little leaf gene 1 heterozygous |
| 12AF.2405 | F1 | isogenic to 2401, little leaf gene 2 heterozygous |
| 12AF.2408 | F1 | F1 of the invention, isogenic to 2401, little leaf gene 1 and 2 heterozygous |

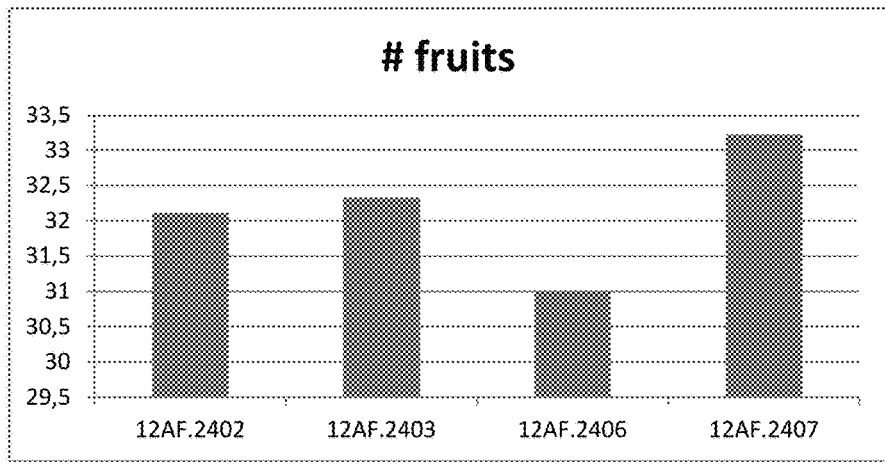

| 12AF.2402 | F1 | no little leaf genes |
| 12AF.2403 | F1 | isogenic to 2402, little leaf gene 1 heterozygous |
| 12AF.2406 | F1 | isogenic to 2402, little leaf gene 2 heterozygous |
| 12AF.2407 | F1 | F1 of the invention, isogenic to 2402, little leaf gene 1 and 2 heterozygous |

CUCUMBER WITH INCREASED NUMBER OF FRUITS

RELATED APPLICATIONS AND INCORPORATION BY REFERENCE

This application claims priority to EP patent application Serial No. 12158714.1 filed 9 Mar. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a cucumber plant (*Cucumis sativus*) which may comprise genetic information that results in an increase in the number of fruits. The invention also relates to the seeds and progeny of such plants and to propagation material for obtaining such plants. Furthermore the invention relates to the use of the plants, seeds and propagation material that may comprise the genetic information as germplasm in a breeding programme.

BACKGROUND OF THE INVENTION

Breeding new vegetable varieties is based on the presumption of the ability of developing new traits or improving existing traits. Traditionally important characteristics for any crop are disease resistances, shelf life, fruit quality, plant vigour, and yield.

Yield increase is among the most complex quantitative traits to acquire. Many processes and interactions with other aspects of plant and fruit development exist, both genetically and environmentally. For example in cucumber, several studies have been done to analyse the various components that may or might contribute to yield. An extra complicating factor in cucumber is the observation that the genetic base of the presently cultivated cucumbers is rather narrow and offers limited room for recombination and improvement (Meglic et al., Genet. Res. Crop Evol. 46:533-546, 1996). This is especially the case for long cucumbers. They may freely be combined with their shorter relatives such as slicers, Beit Alpha types, or picklings, but the genes that may be introduced from those often have a negative effect on plant vigour or on the long cucumber size, and consequently on their high yield.

Yield that may be attained in greenhouse-grown long cucumbers is very high, with around 80 kg/m² as an average in the Netherlands in 2008. Yields for the shorter cucumbers are extremely lower, due to a different type of growing and a shorter growing period, but also due to the genetic potential of the crop. In the US, the average yield for cucumbers (mainly slicers combined with gherkins) in 2008 was around 1.6 kg/m². This indicates the large gap in potential between different growing practices and various types belonging to the same *Cucumis sativus* species.

Although yield is strongly influenced by environmental factors, studies have shown that e.g. number of female nodes and days to anthesis are negatively correlated with yield per plant (López-Sesé and Staub, J. Amer. Soc. Hort. Sci. 127(6): 931-937, 2002), while e.g. larger leaf size and main stem length are positively correlated with yield per plant (fruit mass) (Serquen et al, J. Amer. Soc. Hort. Sci. 122(4): 522-528, 1997).

One approach that could be used in cucumber growing to increase the yield per m² is to plant at a higher density. Increasing the plant density however will need a higher number of plants per area, which means higher costs per area. If a plant as such does not produce a higher yield, there has to be another way of recovering those costs. In addition, closer planting may result in a decrease in light intensity which gives poorer plant and fruit development. The higher number of plants per area often also results in a higher disease incidence because of a change in micro-climate. Plants that are suitable for closer planting, for example plants with smaller leaves, are known to have negative side-effects such as slow growth, poorer fruit quality, or lower yield per plant. In addition, this still means higher costs per area for planting material.

Citation or identification of any document in this application is not an admission that such document is available as prior art to the present invention.

SUMMARY OF THE INVENTION

It is an object of the present invention to provide a cucumber plant (*Cucumis sativus*) which may comprise a combination of genes that results in an increase in the number of fruits per plant.

During the research that resulted in the present invention a combination of genes leading to an increase in the number of fruits of a cucumber plant was found. Against leading assumptions, it was unexpectedly observed that a combination of at least two genes that separately lead to a decrease in leaf size when in homozygous state, gave a higher number of fruits per plant when combined in heterozygous state.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of *Cucumis sativus* EX5005 and 10697156 that comprise a gene combination of the invention which leads to an increase in the number of fruits were deposited. The Deposits with NCIMB Ltd, Ferguson Building, Craibstone Estate, Bucksburn, Aberdeen AB21 9YA, UK, under deposit accession numbers NCIMB 41946 and NCIMB 41947 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

the FIGURE comparison of plants without little leaf genes, isogenic plants each which may comprise one of two different little leaf genes heterozygously, and isogenic plants of the invention which may comprise both said little leaf genes heterozygously.

DETAILED DESCRIPTION OF THE INVENTION

The present invention thus provides a cucumber plant capable of producing an increased number of fruits, wherein the increased number of fruits is caused by a combination of at least two genes that separately in homozygous state result in a reduction of individual leaf surface as compared to an isogenic cucumber plant not carrying either of the said genes, wherein each of the said genes of the said combination is in heterozygous state, and wherein the increased number of fruits is as compared to an isogenic cucumber plant carrying only one or none of the said genes.

The combination of the at least two genes in heterozygous state preferably does not result in a significant reduction of individual leaf surface as is caused by the presence of at least one of said genes in homozygous state.

In one embodiment of the invention, a combination of genes resulting in an increased number of fruits is as present in a cucumber plant which may comprise such a combination of genes, representative seed of which plant is deposited with the NCIMB under deposit number NCIMB 41946 which may comprise a combination of two genes in homozygous state, and NCIMB 41947 which may comprise a combination of two genes in heterozygous state. A combination of genes of the invention is obtainable by introgression from a cucumber plant which may comprise said genes, representative seed of which plant is deposited with the NCIMB under deposit number NCIMB 41946 which may comprise a combination of two genes in homozygous state, and NCIMB 41947 which may comprise a combination of two genes in heterozygous state. The latter combination is a combination of the invention. Plants of seeds of the first deposit are suitable parent plants for producing plants of the invention.

It is well known that in cucumber and other crops a positive correlation exists between larger leaf size and fruit yield per plant. However, during the research that led to the present invention, an uncommon approach to reach the goal of obtaining a higher yield through a higher number of fruits was followed.

Various genes are known to result in small leaves in cucumber. Generally the small leaf types are found in short cucumber types, such as gherkins. Another *Cucumis sativus* with small leaves is the feral subspecies *hardwickii*. The small leaves are determined by single recessive genes. This indicates that in heterozygous state there is no effect of the recessive allele on the leaf size.

When a gene for small leaves is introduced homozygously into a long cucumber type, the reduction in leaf size is significant. However, plants that have a gene resulting in small leaves homozygously are known to have an inferior fruit quality, generally expressed by reduced size, poor seed cavity, and poorer fruit colour. Especially for the long cucumbers, where a high level of internal and external fruit quality is extremely important, these reductions are not acceptable. Internal research has also led to the conclusion that the homozygous introduction of known genes resulting in small leaves leads to a significant reduction in yield for long cucumber types.

However, a different approach was used by the inventors, whereby two different genes that each are known to result in small leaves in homozygous state, were combined in heterozygous state. When one heterozygous gene was introduced in a long cucumber background, the reduction in leaf size was either none or very small, and not significantly so, as was expected for a recessive gene.

The combination of two of the said genes homozygously resulted in an even smaller leaf size than when just one little leaf gene was present homozygously in a long cucumber background. Nevertheless, two genes heterozygously did only give a limited or no decrease in leaf size, again as expected.

Surprisingly however, it was found that the heterozygous introduction of a gene resulting in small leaves did certainly have an effect, in spite of having a negligible effect on leaf size. It was found that the number of fruits of a plant that had a heterozygous gene for small leaves was significantly increased over the number of fruits of an isogenic plant lacking this gene. In addition, there was an average increase in the yield per plant, or yield (kg) per $m^2$ (Tables 1 and 2).

Continuing studies were undertaken in which not only one, but two genes resulting in small leaves were combined heterozygously into a cucumber plant. When two genes resulting in the same trait are combined, the chances are that the trait is expressed as it would when only one of those genes is present, for example since they both affect the same pathway at the same step, or because the optimum value of a trait has been reached. Another option is that the genes interfere so that the final expression is decreased as compared to the expression when only one of the genes is present. It is certainly not a matter of course that an additive effect would be obtained.

Remarkably, it was determined that the combination of two heterozygous little leaf genes resulted in a higher number of fruits per plant as compared to a plant that comprised only one heterozygous gene for little leaves.

In a preferred embodiment the combination of the at least two genes in heterozygous state results in a higher increase in the number of fruits than the sum of the separate increases in the number of fruits of plants which may comprise either one of the at least two genes in heterozygous state. The combination of two little leaf genes thus has a synergistic effect.

During research that followed, the effect of the combination of two genes was further investigated. Results showed that in certain cases the higher number of fruits for the double heterozygous plants did not only amount to the sum of both increases separately, which is extraordinary in itself, but a heterosis effect could be obtained resulting in an increase that was higher than the increases separately (Tables 1 and 2). The same effect was found for the yield per plant or per m².

TABLE 1

Yield comparison of Cucumber varieties having none, 1, or 2 genes for small leaves heterozygously

| Variety | frts/m² | kg/m² | av. frt wt (g) | % incr frts/m² | % incr kg/m² |
|---|---|---|---|---|---|
| Autumn 2006 | | | | | |
| A | 50.3 | | | | |
| B | 52.1 | | | 4% | |
| Summer 2006 | | | | | |
| A | 47.6 | 23.3 | 490 | | |
| B | 49.9 | 23.1 | 463 | 5% | −1% |
| Spring 2007 | | | | | |
| C | 85.3 | 36.8 | 431 | | |
| D | 92.9 | 38.4 | 413 | 9% | 4% |
| Summer 2007 | | | | | |
| C | 52.2 | 25.1 | 481 | | |
| D | 55.9 | 26.2 | 468 | 7% | 4% |
| Summer 2007 | | | | | |
| C | 56.9 | 25.8 | 453 | | |
| D | 58.6 | 25.4 | 434 | 3% | 2% |
| Autumn 2011 | | | | | |
| E | 38.2 | 16.8 | 440 | | |
| F | 40.3 | 17.1 | 424 | 5% | % |
| G | 44.3 | 18.1 | 408 | 16% | 8% |
| Summer 2011 | | | | | |
| E | 54.9 | 25.9 | 471 | | |
| F | 60.5 | 28.0 | 463 | 10% | 8% |
| G | 66.8 | 28.5 | 427 | 22% | 10% |
| Summer 2011 | | | | | |
| | 61.1 | 26.9 | 440 | | |
| G2 | 64.5 | 27.1 | 420 | 6% | 1% |

A: F1 plant, no genes for small leaves (AABB)
B: Isogenic plant of A, 1 heterozygous gene (AaBB) for small leaves
C: F1 plant, no genes for small leaves (AABB)
D: Isogenic plant of C, 1 heterozygous gene (AABb) for small leaves
E: Standard F1 plant, no genes for small leaves (AABB)
F: F1 plant with 1 heterozygous gene (AaBB) for small leaves
G and G2: F1 plant with 2 heterozygous genes (AaBb) for small leaves
Increase of B is as compared to A, increase of D as compared to C, increase of F as compared to E, increase of G as compared to E, increase of G2 as compared to F. Comparisons for increase were done within the same trial.

TABLE 2

Average increases per heterozygous gene

| | fruits/m² | kg/m² |
|---|---|---|
| Average increase Aa | 6% | 3.5% |
| Average increase Bb | 6% | 3% |

TABLE 2-continued

Average increases per heterozygous gene

| | fruits/m² | kg/m² |
|---|---|---|
| Average increase AaBb | 19% | 9% |
| Average increase AaBb as compared to AaBB | 10% | 3% |

Increases are as compared to AABB, unless mentioned differently

In one embodiment, the invention relates to a method for increasing the number of fruits of a cucumber plant which may comprise combining at least two genes that separately, when in homozygous state, result in a reduction of individual leaf surface as compared to an isogenic cucumber plant not carrying either of the said genes, wherein each of the said genes of the said combination of the invention is in heterozygous state. A gene that, when present in homozygous stage, results in a reduction of individual leaf surface as compared to an isogenic cucumber plant not carrying the said gene is called herein "little leaf gene".

In a further embodiment, the invention relates to the said method for increasing the number of fruits wherein the combination of the at least two little leaf genes in heterozygous state results in a higher increase in the number of fruits than the sum of the increases of the at least two little leaf genes separately.

Several genes are known that lead to a significant reduction in leaf size when they are present in homozygous state, i.e. these little leaf genes are recessive. To reach a plant of the invention, having an increase in the number of fruits due to a combination of two of those genes in heterozygous state, it is irrelevant which of the said little leaf genes are combined. Any two or more genes that homozygously, when separate or combined, result in small leaves, will result in an increase in the number of fruits when combined heterozygously, according to the research that resulted in the invention. When combined heterozygously the plants will not have small leaves as found when one or more genes are present homozygously.

In one embodiment, the invention relates to a product for increasing the number of fruits of a recipient cucumber plant, wherein the product may comprise at least two genetic determinants in heterozygous state, which genetic determinants when separately present in the genome of a cucumber plant in homozygous state result in a reduction of individual leaf surface as compared to an isogenic cucumber plant not carrying either of the said genetic determinants. The product is in its most basic form a DNA sequence which may comprise two little leaf genes or a combination of two DNA sequences that each comprise one little leaf gene. The DNA sequence may be a locus, gene, allele but also a vector which may comprise two little leaf genes or even a plant which may comprise two little leaf genes. The DNA sequences and vectors when in isolated form may be used for transgenically or cisgenically increasing the number of fruits produced by a recipient plant. When the product is a plant this may be done by introgression. In a preferred embodiment, the product may comprise the two little leaf genes in homozygous form. An example of such product is a plant grown from seed of which a representative sample was deposited under deposit accession number NCIMB 41946.

When a gene that homozygously results in small leaves is identified, it is possible through regular research known to the skilled person to develop molecular markers to follow the presence of this gene through subsequent generations, even when the phenotype does not express the heterozygous state. When two or more of those genes are combined, the use of molecular markers may identify plants of the invention that comprise at least two genes in heterozygous state.

Two genes that result in small leaves when present in homozygous state are homozygously present in the deposit NCIMB 41946. Deposit number NCIMB 41947 may comprise two of said genes in heterozygous state. The presence of the combination of those genes in heterozygous state leads to an increase of the number of fruits per plant. The presence of the combination of those genes in heterozygous state preferably does not lead to small leaves as caused by the presence of at least one of said genes in homozygous state. To introgress the genes, suitably a cross is made between a plant carrying said genes homozygously, representative seed of which is deposited as NCIMB 41946, and another plant not carrying the said genes. The resulting F1 is a plant of the invention which may comprise two genes for little leaf in heterozygous state and producing an increased number of fruits as compared to the parent that has the two genes homozygously and the parent that does not have the genes. The increase in the number of fruits suitably results in an increase in the yield, i.e. in $kg/m^2$.

Alternatively, a cross may be made between a plant carrying two genes in heterozygous state, representative seed of which is deposited as NCIMB 41947, and another plant not carrying genes for little leaf. In the resulting F1 plants may be identified carrying two genes heterozygously, suitably by using molecular markers linked to the said genes.

Alternatively, other genes resulting in small leaves may be used from other sources. Possible genes resulting in a combination of the invention could for example be the "little leaf" (ll) gene (Goode et al, Ark. Farm Res. 29:4, 1980), the "compact" gene (cp) (Kauffman and Lower, J. Amer. Soc. Hort. Sci. 101:150-151, 1976), the "compact-2" gene (cp-2) (Kubicki et al., Genetica Polonica 27:289-298, 1986), the gene causing small leaves of the wild cucumber relative *Cucumis sativus* var. *hardwickii*, genes causing small leaves in gherkin types of *Cucumis sativus*, or any other known or yet to be identified non-dominant gene resulting in small leaves in *Cucumis sativus*.

"Small leaves" or "little leaves" as used herein are leaves that have a reduction in individual leaf surface of, in order of increased preference, at least 10%, at least 20%, at least 30%, at least 40%, at least 50%, at least 60%, at least 70%, at least 80% as a result of the homozygous presence of one of the said genes.

"Introgression" as used herein is intended to mean introduction of a gene into a plant not carrying the gene by means of crossing, and selection in the first generation in which the trait becomes visible. Preferably, selection is done with the assistance of molecular markers that are linked to the genes. Marker assisted selection may be done in any generation or population that may comprise plants carrying any number of desired genes.

It is clear that the parent that provides one or more genes that result in a plant of the invention is not necessarily a plant grown directly from the deposited seeds. The parent may also be a progeny plant from the seed, or a progeny plant from seeds that are identified to have a gene of the invention by other means.

In one embodiment, two sources that each have one gene resulting in small leaves may be crossed, and in the resulting F1 or subsequent generations plants that comprise two genes heterozygously may be identified, preferably by using molecular markers related to said genes.

According to the invention, a product for increasing the number of fruits of a recipient cucumber plant may comprise at least two genetic determinants in heterozygous state, which genetic determinants when separately present in homozygous state result in small leaves, wherein any one of the genetic determinants comprised in the product is selected from a group which may comprise: a gene, an allele, a gene construct, a QTL, a promoter, an isolated gene, a transgene, a DNA sequence.

The invention furthermore relates to a cell of a cucumber plant as claimed. Such cell may be either in isolated form or may be part of the complete cucumber plant or parts thereof and then still constitutes a cell of the invention because such a cell harbours in its genetic constitution the genetic information that leads to the characteristics that define the cucumber plant of the invention. Each cell of cucumber plants of the invention carries the genetic information that leads to phenotypic expression of said trait. Such a cell of the invention may also be a regenerable cell that may be used to regenerate a new cucumber plant of the invention. A cell of the present invention carries at least two little leaf genes in heterozygous state.

The invention also relates to tissue of a plant as claimed. The tissue may be undifferentiated tissue or already differentiated tissue. Undifferentiated tissues are for example stem tips, anthers, petals, pollen and may be used in micropropagation to obtain new plantlets that are grown into new plants of the invention. The tissue may also be grown from a cell of the invention. The cells of the tissue of the present invention carry at least two little leaf genes in heterozygous state.

The invention according to a further aspect thereof relates to seeds of a plant as claimed. Although the seeds do not show the genetic trait of the cucumber plant of the invention, they harbour the genetic information that when a plant is grown from the seeds makes this plant a plant of the invention. The seeds of the invention carry in their genome at least two little leaf genes in heterozygous state.

The invention also relates to progeny of the plants, cells, tissues and seeds of the invention. Such progeny may in itself be plants, cells, tissues or seeds. Progeny plants of the invention carry at least two little leaf genes in heterozygous state and as a result have an increased number of fruits as compared to plants not carrying at least two little leaf genes in heterozygous state.

As used herein the word "progeny" is intended to mean the first and all further descendants from a cross with a plant of the invention that may comprise a combination of at least two genes that leads to an increase in the number of fruits per plant. Progeny of the invention are descendants of any cross with a plant of the invention that carries the combination of at least two little leaf genes that leads to an increase in the number of fruits when the genes are heterozygously present.

"Progeny" also encompasses plants that carry the combination of little leaf genes that causes an increase in the number of fruits wherein the genes are obtained from other plants or progeny of plants of the invention by vegetative propagation or multiplication.

The invention thus further relates to seed of the claimed plant and to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, and protoplasts.

According to a further aspect thereof the invention provides a tissue culture of the claimed plant. The tissue culture may comprise regenerable cells. Such tissue culture may be derived from leaves, pollen, embryos, cotyledons, hypocotyls, meristematic cells, roots, root tips, anthers, flowers, seeds and stems. The tissue culture may be regenerated into a plant carrying the combination of genes of the invention. Suitably a regenerated plant expresses the phenotype of increase number of fruits as compared to an isogenic plant not carrying the combination of genes heterozygously.

The invention furthermore relates to hybrid seed and to a method of producing hybrid seed which may comprise crossing a first parent plant with a second parent plant and further harvesting the resultant hybrid seed, wherein said first parent plant has at least one little leaf gene in homozygous state and the second parent plant has one or more other little leaf genes in homozygous state, or either the first parent plant or the second parent plant has the combination of at least two little leaf genes homozygously, while the other parent plant does not carry those same genes. The resulting hybrid plant is then a plant as claimed.

In one embodiment, the invention relates to cucumber plants of the invention that carry the combination of genes of the invention which leads to an increase in the number of fruits, and that have acquired said genes by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the combination of genes of the invention is acquired is formed by plants grown from seeds of which a representative sample was deposited under accession number NCIMB 41946, or from seeds of which a representative sample was deposited under accession number NCIMB 41947, or from the deposited seeds NCIMB 41946 or NCIMB 41947, or from sexual or vegetative descendants thereof, or from another source which may comprise one or more genes for little leaf, in particular the genes as present in the deposits, or from a combination of these sources.

In a preferred embodiment, the invention relates to non-transgenic *Cucumis sativus* plants. The source for acquiring one or more of the genes of the combination of the invention, to obtain a plant of the invention that has an increase in the number of fruits, is suitably a *Cucumis sativus* plant that carries the genes as comprised in NCIMB 41946 or NCIMB 41947, or alternatively a plant of a *Cucumis* species that carries one or more of the said genes and that may be crossed with *Cucumis sativus*. Optionally after crossing with a related species techniques such as embryo rescue, back-crossing, or other techniques known to the skilled person may be performed to obtain seeds of the interspecific cross, which seeds may be used as the source for further development of a non-transgenic *Cucumis sativus* plant that shows an increase in the number of fruits due to a heterozygous combination of at least two genes that separately and in combination result in a reduced leaf size when in homozygous state.

The invention also relates to the germplasm of plants of the invention. The germplasm is constituted by all inherited characteristics of an organism and according to the invention encompasses at least the trait of the invention. The germplasm may be used in a breeding programme for the development of cucumber plants having an increase in the number of fruits. The germplasm of the invention may comprise at least two little leaf genes. The germplasm of the invention may comprise the little leaf genes in heterozygous state and then constitutes germplasm that is capable of expressing the trait of an increased number of fruits. Alternatively, the germplasm may comprise the at least two little leaf genes in homozygous state and then constitutes germplasm that may be used in breeding for plants of the invention or for the production of hybrid cucumber plants that have an increased fruit yield.

The invention also relates to a cucumber fruit that is produced by a plant of the invention. The invention further relates to a food product, which may comprise the fruit of a cucumber plant as claimed, or parts thereof. The invention also relates to a food product in processed form. The fruit or food product of the invention may comprise the novel heterozygous combination of the invention of at least two genes that when homozygously present result in small leaves.

In one aspect the invention relates to a method for production of a cucumber plant which may comprise a combination of at least two genes that in heterozygous state lead to an increase in the number of fruits, which may comprise:

a) crossing a plant which may comprise a combination of two genes that result in an increase in the number of fruits, representative seed of which was deposited as NCIMB 41946, with a plant not which may comprise the genes to obtain an F1 population; b) optionally performing one or more rounds of selfing and or crossing a plant from the F1 to obtain a further generation population;

b) selecting a plant that may comprise a heterozygous combination of two little leaf genes that result in an increase in the number of fruits, suitably by using molecular markers linked to the little leaf genes.

The invention additionally provides a method of introducing a desired trait into a cucumber plant capable of producing an increased number of fruits as a result of the combination in its genome of at least two little leaf genes, which may comprise:

a) crossing a cucumber plant which may comprise a combination of at least two little leaf genes that lead to an increase in the number of fruits, representative seed of which were deposited with the NCIMB under deposit number NCIMB 41946, with a second cucumber plant that may comprise a desired trait to produce F1 progeny;

b) selecting an F1 progeny that produces an increased number of fruits and has the desired trait;

c) crossing the selected F1 progeny with either parent, to produce backcross progeny;

d) selecting backcross progeny which may comprise the desired trait and producing an increased number of fruits; and e) optionally repeating steps c) and d) one or more times in succession to produce selected fourth or higher backcross progeny that may comprise the desired trait and the combination of at least two little leaf genes heterozygously, which combination leads to an increase in the number of fruits per plant. The invention includes a cucumber plant produced by this method and the cucumber fruit obtained therefrom.

Selection for a plant which may comprise the combination of little leaf genes of the invention may alternatively be done following any crossing or selfing step of the method.

In one embodiment the plant which may comprise the combination of little leaf genes either homozygously or heterozygously is a plant of an inbred line, a hybrid, a doubled haploid, or of a segregating population.

The invention further provides a method for the production of a cucumber plant capable of producing an increased number of fruits by using a doubled haploid generation technique to generate a doubled haploid line that homozygously may comprise the said combination of little leaf genes that leads to an increase in the number of fruits, which doubled haploid line may be crossed with a line that lacks the said genes to generate a plant of the invention that may comprise the combination of little leaf genes heterozygously.

The invention furthermore relates to hybrid seed and to a method for producing hybrid seed which may comprise crossing a first parent plant with a second parent plant and harvesting the resultant hybrid seed, wherein said first parent plant and/or said second parent plant is a plant that may comprise the one or more little leaf genes that result in a plant of the invention homozygously, and the resulting hybrid is a plant as claimed.

The invention also relates to a method for the production of a cucumber plant capable of producing an increased number of fruits, which plant may comprise a combination of at least two genes heterozygously, which genes in homozygous state result in a reduced leaf size, by using a seed that may comprise the combination of genes in its genome that leads to an increase in the number of fruits for growing the said cucumber plant. The seeds are suitably seeds of which representative samples were deposited with the NCIMB under deposit numbers NCIMB 41946 and NCIMB 41947.

The invention also relates to a method for seed production which may comprise growing cucumber plants which may comprise a combination of at least two little leaf genes heterozygously, which combination results in an increase in the number of fruits, allowing the plants to produce seeds, and harvesting those seeds. Production of the seeds is suitably done by crossing or selling.

In one embodiment, the invention relates to a method for the production of a cucumber plant which may comprise an increase in the number of fruits as a result of the heterozygous presence of at least two little leaf genes by using tissue culture. The invention furthermore relates to a method for the production of a cucumber plant which may comprise an increase in the number of fruits as a result of a heterozygous combination of at least two genes that lead to a reduced leaf size when homozygous, by using vegetative reproduction.

In one embodiment, the invention relates to a method for the production of a cucumber plant which may comprise an increase in the number of fruits by using a method for genetic modification to introduce a combination of genes of the invention, which combination leads to an increase in the number of fruits, into the cucumber plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of cucumber plants that comprise a heterozygous combination of at least two genes that each lead to a reduction in leaf size when homozygously present, wherein germplasm which may comprise a gene that leads to a reduction in leaf size is used. Preferably, germplasm with a combination of at least two little leaf genes is used. Representative seed of said plant which may comprise a combination of two little leaf genes in homozygous state was deposited with the NCIMB under deposit number NCIMB 41946.

In a further embodiment the invention relates to a method for the production of a cucumber plant which may comprise a heterozygous combination of at least two genes that each lead to a reduction in leaf size when in homozygous state, wherein progeny or propagation material of a plant which may comprise a combination of at least two little leaf genes that when heterozygously present confers an increase in the number of fruits is used as a source to introgress at least two little leaf genes into another cucumber plant. Representative seed of said plant which may comprise a combination of said genes in homozygous state was deposited with the NCIMB under deposit number NCIMB 41946. Representative seed of a plant which may comprise a combination of said genes in heterozygous state was deposited as NCIMB 41947.

The invention provides preferably a cucumber plant showing an increase in the number of fruits due to a heterozygous combination of at least two genes that when present in homozygous state result in a reduction in leaf size, which plant is obtainable by any of the methods herein described.

The invention also relates to a method for the production of cucumber fruits, which may comprise growing cucumber plants with a combination of at least two little leaf genes, which combination leads to an increase in the number of fruits as described herein and allowing them to produce cucumber fruits and optionally harvesting the fruits.

A gene may be identified by the use of a molecular marker. A gene may alternatively be identified by the position on a genetic map, or by indication of the location on a linkage group or chromosome. When a gene is not linked to a specific molecular marker any longer, but its position on a chromosome as defined on a genetic map is unaltered, this gene is still the same as when it was linked to the molecular marker. The genetic trait that it confers is therefore also still the same.

The 'genetic trait' is the trait or characteristic that is conferred by the gene. In the present invention the trait is the increase in fruit number and/or fruit yield and the gene is the combination of at least two little leaf genes in heterozygous state. The genetic trait may be identified phenotypically, for example by performing a bio-assay. However, also plant stages for which no phenotypic assay may be performed do carry the genetic information that leads to the genetic trait. 'Trait' or 'phenotypic trait' may be used instead of 'genetic trait'. Furthermore, in case of a heterozygous trait homozygous plants also carry genetic information that when present in heterozygous form causes the increase in the number of fruits. Such plants are a source of the genes or alleles and as such are also part of this invention.

In the absence of molecular markers, or in the instance that recombination between the gene(s) and the marker has taken place so that the marker is not predictive anymore, equivalence of genes may be determined by an allelism test. To perform an allelism test, a tester plant which is homozygous for the known gene of the invention is crossed with material to be tested that is also homozygous for its gene. When no segregation for the trait to be observed is present in the F2 of the cross, the genes have been proven to be equivalent or the same.

When more than one gene is responsible for a certain trait, and an allelism test is done to determine equivalence, the skilled person doing the test has to make sure that all relevant genes are present homozygously for the test to work properly.

The invention will be further illustrated in the Examples that follow.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Creation of Cucumber Plants of the Invention

A cross was made between plants from two different internal breeding lines from *Cucumis sativus* (cucumber), KK5.763 and KK5.735. Each line comprised a different gene in homozygous state, which gene in this state causes a significant decrease in leaf size. Therefore each of these lines was a line with small leaves, but with a different gene determining the small leaves. KK5.763 may be represented by aaBB and KK5.735 by AAbb. The presence of the recessive genes causes the small leaf phenotype. Both parents therefore have small leaves, or little leaves.

In the F1 progeny 10697156 of KK5.763×KK5.735, which may be represented as aaBB×AAbb, and the F1 10697156 as AaBb, plants with unexpected new characteristics were obtained. Comparing the plants of F1 10697156 to control plants from cucumber lines not having genes causing small leaves, showed that in the F1 a large increase of 16% in fruits/$m^2$ was obtained. Even though the fruits of plants of the invention were slightly smaller than fruits from plants without little leaf genes, the increase in number of fruits still resulted in an increase in yield (kg/$m^2$) of approximately 8%.

Little leaf genes are recessive genes, therefore plants having one little leaf gene homozygously have a significant decrease in individual leaf surface. Plants which may comprise one little leaf gene heterozygously do not have such a significant decrease in individual leaf surface as found in plants having said gene homozygously. Plants having two of said genes heterozygously, which are plants of the invention, also do not have a significant decrease in individual leaf surface as found in plants having one of said genes homozygously.

Plants having two little leaf genes homozygously have very small leaves, even smaller than plants which may comprise one of said genes homozygously. These plants are regarded to have too small leaves to be feasible for cucumber production in practice.

Subsequent trials confirmed the increase in number of fruits and the increase in kg/$m^2$ of the plants of the invention having two genes heterozygously, which genes cause small leaves when present in homozygous state.

Seeds from the F1 10697156 were deposited under number NCIMB 41947.

Example 2

Characterization of the Invention

Plants of the invention, representative seeds of which were deposited as NCIMB 41947, were compared with cucumber plants without the combination of the invention, having only one or no gene causing small leaves. Table 1 and Table 2 show the results of this comparison.

From the results in Table 1 it may be learned that cucumber plants that have one heterozygous gene for small leaves (varieties B, D, and F) result on average in more fruits/$m^2$, compared to isogenic plants or control plants without any genes for small leaves (varieties A, C, and E). The cucumber plants of the invention having two heterozygous genes for small leaves (variety G) produce on average more fruits/$m^2$ than its counterpart with only one heterozygous gene (variety F), and far more than a control plant without any genes for small leaves (variety E).

In Table 2 the results from Table 1 are summarized. The average increase of fruits/$m^2$ of cucumber plants with two heterozygous genes for small leaves compared to cucumber plants without small leaf genes is 19%. The average yield increase (kg/$m^2$) is 9%. The plants within each trial were planted at the same planting distance.

Further observations in different genetic cucumber backgrounds which represent different breeding lines were made to confirm the increase in number of fruits in plants of the invention. The heterozygous presence of a combination of two little leaf genes was compared in different crosses, wherein comparison was made with a cross that had both parents without little leaf genes, and crosses that had only one of the parents with a little leaf gene. The increase was determined at 5 weeks after the first harvest of fruits was started (the FIGURE, Table 3).

TABLE 3

|  | week 42-47 cumm # fruits | % increase # fruits compared to 2401 | sum increase |
|---|---|---|---|
| 12AF.2401 | 34.33 |  |  |
| 12AF.2404 | 39.66 | 15.53% |  |
| 12AF.2405 | 34.61 | 0.82% | 16.34% |
| 12AF.2408 | 40.33 | 17.48% |  |

12AF.2401 F1, no little leaf genes
12AF.2404 F1, isogenic to 2401, little leaf gene 1 heterozygous
12AF.2405 F1, isogenic to 2401, little leaf gene 2 heterozygous
12AF.2408 F1 of the invention, isogenic to 2401, little leafgene 1 and 2 heterozygous

|  | week 42-47 cumm # fruits | % increase # fruits compared to 2402 | sum increase |
|---|---|---|---|
| 12AF.2402 | 32.11 |  |  |
| 12AF.2403 | 32.33 | 0.69 |  |
| 12AF.2406 | 31.00 | −3.46 | −2.77 |
| 12AF.2407 | 33.22 | 3.46 |  |

12AF.2402 F1, no little leaf genes
12AF.2403 F1, isogenic to 2402, little leaf gene 1 heterozygous
12AF.2406 F1, isogenic to 2402, little leaf gene 2 heterozygous
12AF.2407 F1 of the invention, isogenic to 2402, little leaf gene 1 and 2 heterozygous Example 3

Transfer of the Trait to Other Cucumber Plants

Plants of EX5005, representative seed of which were deposited under NCIMB accession number 41946, having two genes for small leaves in a homozygous state (aabb), were crossed with various cucumber breeding lines (AABB), for example internal line KK5.588, not having said genes, to obtain F1 seed (AaBb). The F1 seed was sown subsequently and F1 plants were grown. The F1 plants were allowed to self and F2 seed was obtained and sown. The F2 progeny segregated for plants having none, one or two genes for little leaves either in homozygous state or in heterozygous state.

In the F2 progeny approximately 25% of the plants showed the same genotype as the F1, and as a plant of the invention, AaBb. Those plants were selected that showed the same characteristics as the plant of the invention NCIMB 41947. Plants having the genotype of the invention were phenotypically indistinguishable from plants having normal leaves, but they were producing more fruits per square meter as compared to plants having one gene in a heterozygous form for small leaves, and as compared to plants not having genes for small leaves. Molecular markers were used to identify plants which may comprise two little leaf genes in heterozygous state in an early stage. Further development of these plants resulted in lines with the trait of the invention as found in NCIMB 41947.

The invention is further described by the following numbered paragraphs:

1. A cucumber plant capable of producing an increased number of fruits wherein the increased number of fruits is caused by a combination of at least two genes that separately in homozygous state result in a reduction of individual leaf surface as compared to an isogenic cucumber plant not carrying either of the said genes, wherein each of the said genes of the said combination is in heterozygous state, and wherein the increased number of fruits is as compared to an isogenic cucumber plant carrying only one or none of the said genes.

2. A cucumber plant according to paragraph 1, wherein the combination of at least two genes in heterozygous state does not result in a significant reduction of individual leaf surface as is caused by the presence of at least one of said genes in homozygous state.

3. A cucumber plant according to paragraph 1 or 2, wherein a combination of genes is as present in a cucumber plant comprising said genes, representative seed of which plant is deposited with the NCIMB under deposit numbers NCIMB 41946 comprising two genes in homozygous state and NCIMB 41947 comprising two genes in heterozygous state.

4. A cucumber plant according to any one of the paragraphs 1 to 3, wherein the combination of the at least two genes in heterozygous state results in a higher increase in the number of fruits than the sum of the separate increases in the number of fruits of plants comprising either one of the at least two genes in heterozygous state.

5. Product for increasing the number of fruits of a recipient cucumber plant, wherein the product comprises at least two genetic determinants in heterozygous state, which genetic determinants when separately present in homozygous state in the genome of a cucumber plant result in a reduction of individual leaf surface as compared to an isogenic cucumber plant not carrying either of the said genetic determinants, and wherein any one of the genetic determinants comprised in the product is selected from a group comprising: a gene, an allele, a gene construct, a QTL, a promoter, an isolated gene, a transgene, a DNA sequence.

6. Product according to paragraph 5, wherein the combination of genetic determinants is as present in a cucumber plant comprising said genetic determinants, representative seed of such plant having been deposited with the NCIMB under deposit numbers NCIMB 41946 comprising two genes in homozygous state and NCIMB 41947 comprising two genes in heterozygous state.

7. Seed of a cucumber plant according to any one of the paragraphs 1-4, wherein the plant that may be grown from the seed comprises the combination of genes as defined in any one of the claims 1 to 4.

8. Progeny of a cucumber plant according to any one of the paragraphs 1-4 or of cucumber seed according to paragraph 7 comprising the combination of genes as defined in any one of the paragraphs 1 to 4.

9. Propagation material suitable for producing a plant according to any one of the paragraphs 1-4 or 8 or for producing seed according to paragraph 7, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledon, hypocotyls, meristematic cells, roots, root tips, anthers, flowers, seeds and stems, wherein a plant produced from the propagation material comprises the combination of genes as defined in any one of the paragraphs 1 to 4.

10. A cucumber fruit of a plant according to any one of the paragraphs 1-4 or 8, which fruit comprises the combination of genes as defined in any of the paragraphs 1 to 4 in its genome.

11. Food product, comprising the cucumber fruit according to paragraph 10, or parts thereof, optionally in processed form, which food product comprises the combination of genes as defined in any of the paragraphs 1 to 4 in its genome.

12. Use of a plant according to any one of the paragraphs 1-4 or 8, or plants produced from the seeds of paragraph 7, or from the propagation material according to paragraph 9 as germplasm in a breeding programme for the development of cucumber plants with an increase in the number of fruits per plant.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method of producing a hybrid cucumber seed that when said seed is grown into a plant, said plant exhibits an increased number of fruit of at least 16% or an average increased fruit yield of approximately 8% or 9% kg/m$^2$ as compared to an isogenic cucumber plant carrying none of the small leaf genes, or an average increased fruit yield of about 4% kg/m$^2$ as compared to an isogenic cucumber plant carrying only one of the small leaf genes, wherein the small leaf genes are present homozygously in a cucumber plant, representative seed of which plant is deposited with the NCIMB under deposit number NCIMB 41946, said method comprising
crossing a first parent cucumber plant with a second parent cucumber plant and harvesting the resultant hybrid cucumber seed;
wherein:
said first parent cucumber plant has a first small leaf gene of *Cucumis sativus* var. *hardwickii* in homozygous state and the second parent cucumber plant has a second small leaf gene of gherkin type of *Cucumis sativus* in homozygous state, and said first small leaf gene from *Cucumis sativus* var. *hardwickii* and said second small leaf gene from the gherkin type of *Cucumis sativus* are as present homozygously in a cucumber plant, representative seed of which plant is deposited with the NCIMB under deposit number NCIMB 41946, or either the first cucumber parent plant or the second cucumber parent plant has the combination of the first small leaf gene from *Cucumis sativus* var. *hardwickii* and the second small leaf gene from the gherkin type of *Cucumis sativus* homozygously as present in a cucumber plant, representative seed of which plant is deposited with the NCIMB under deposit number NCIMB 41946 while the other parent plant does not comprise the combination of the first small leaf gene from *Cucumis sativus* var. *hardwickii* and the second small leaf gene from the gherkin type of *Cucumis sativus* homozygously as present in a cucumber plant, representative seed of which plant is deposited with the NCIMB under deposit number NCIMB 41946; and the first small leaf gene from *Cucumis sativus* var. *hardwickii* and the second small leaf gene from the gherkin type of *Cucumis sativus* are present in the resultant hybrid seed as present in a cucumber plant, representative seed of which plant is deposited with the NCIMB under deposit number NCIMB 41947; and a small leaf gene is a gene that results in a reduction of individual leaf surface of at least 20% when homozygously present as compared to the isogenic cucumber plant, whereby:

the resultant hybrid cucumber seed comprises the first small leaf gene in a heterozygous state, the second small leaf gene in a heterozygous state, or the first and second small leaf genes in a heterozygous state; and the plant grown from the resultant hybrid cucumber seed exhibits the increased number of fruit of at least 16% or the average increased fruit yield of approximately 8% or 9% kg/m$^2$ as compared to the isogenic cucumber plant carrying none of the small leaf genes or the average increased fruit yield of about 4% kg/m$^2$ as compared to an isogenic cucumber plant carrying only one of the small leaf genes, wherein the small leaf genes are present homozygously in a cucumber plant, representative seed of which plant is deposited with the NCIMB under deposit number NCIMB 41946.

2. The method of claim 1 wherein the first parent cucumber plant has the first small leaf gene of *Cucumis sativus* var. *hardwickii* in homozygous state and the second parent cucumber plant has the second small leaf gene of gherkin type of *Cucumis sativus* in homozygous state, and said first small leaf gene from *Cucumis sativus* var. *hardwickii* and said second small leaf gene from the gherkin type of *Cucumis sativus* are as present homozygously in a cucumber plant, representative seed of which plant is deposited with the NCIMB under deposit number NCIMB 41946.

3. The method of claim 1 wherein either the first parent cucumber plant or the second parent cucumber plant has the combination of the first small leaf gene from *Cucumis sativus* var. *hardwickii* and the second small leaf gene from the gherkin type of *Cucumis sativus* homozygously as present in a cucumber plant, representative seed of which plant is deposited with the NCIMB under deposit number NCIMB 41946, while the other parent plant does not comprise the combination of the first small leaf gene from *Cucumis sativus* var. *hardwickii* and the second small leaf gene from the gherkin type of *Cucumis sativus* homozygously as present in a cucumber plant, representative seed of which plant is deposited with the NCIMB under deposit number NCIMB 41946.

4. The method of claim 1 further comprising growing the resultant hybrid plant and obtaining cucumber therefrom.

5. The method of claim 4 further comprising preparing a food product comprising the cucumber.

6. The method of claim 5 wherein the food product comprising the cucumber comprises a processed food.

* * * * *